(12) United States Patent
Leiboff (10) Patent No.: US 11,006,957 B1
(45) Date of Patent: May 18, 2021

(54) METHOD FOR MAINTAINING SUCTION IN BODY CAVITIES

(71) Applicant: Arnold Leiboff, Old Field, NY (US)

(72) Inventor: Arnold Leiboff, Old Field, NY (US)

( * ) Notice: Subject to any disclaimer, the term of this patent is extended or adjusted under 35 U.S.C. 154(b) by 288 days.

(21) Appl. No.: 16/231,713

(22) Filed: Dec. 24, 2018

Related U.S. Application Data (63) Continuation-in-part of application No. 15/152,778, filed on May 12, 2016, now abandoned.

(60) Provisional application No. 62/162,540, filed on May 15, 2015.

(51) Int. Cl.
| | |
|---|---|
| *A61B 17/11* | (2006.01) |
| *A61M 1/00* | (2006.01) |
| *A61B 17/115* | (2006.01) |
| *A61B 17/12* | (2006.01) |
| *A61B 17/22* | (2006.01) |
| A61B 17/30 | (2006.01) |
| A61B 5/00 | (2006.01) |

(52) U.S. Cl.
CPC ......... *A61B 17/1114* (2013.01); *A61B 17/115* (2013.01); *A61B 17/12099* (2013.01); *A61B 17/22* (2013.01); *A61B 5/4255* (2013.01); *A61B 2017/1139* (2013.01); *A61B 2017/22069* (2013.01); *A61B 2017/306* (2013.01); *A61B 2217/005* (2013.01); *A61M 1/008* (2013.01)

(58) Field of Classification Search
CPC ...... A61B 2217/005; A61B 2017/1139; A61B 2017/22069; A61B 2017/306; A61B 5/4255; A61B 17/1114; A61B 17/115; A61B 17/12099; A61B 17/22
See application file for complete search history.

(56) References Cited

U.S. PATENT DOCUMENTS

| | | | |
|---|---|---|---|
| 4,344,435 A | | 8/1982 | Aubin |
| 4,735,607 A | * | 4/1988 | Keith, Jr. ............... F16K 15/148 137/526 |
| 5,273,523 A | | 12/1993 | Sozuki et al. |

(Continued)

FOREIGN PATENT DOCUMENTS

| | | |
|---|---|---|
| WO | 2015052720 A1 | 4/2015 |
| WO | 2017070691 A1 | 4/2017 |

OTHER PUBLICATIONS

GastriSail™ Gastric Positioning System, www.medtronic.com, printed Jul. 3, 2017.

*Primary Examiner* — Nathan R Price
*Assistant Examiner* — Tasnim Mehjabin Ahmed
(74) *Attorney, Agent, or Firm* — Brian Roffe (57) ABSTRACT

Method for introducing and maintaining a level of negative pressure in a body cavity of at least 80 mmHg using a tube having an elongate distal portion and a proximal portion having first and second arms, each arm having a lumen in flow communication with one another and with the body cavity via apertures at or near the distal end of the tube, wherein the first arm or tubular extension therefrom is adaptable to receive suction from a suction source. An indicator, arranged in relation to the second arm, signals when a specific negative pressure has been exceeded in the tube, or a valve, arranged in relation to the second arm, admits ambient air into the lumen of the second arm when suction is applied to the tube and differential air pressure between the air in the lumens of the tube and ambient air exceeds a specified amount.

20 Claims, 6 Drawing Sheets

(56) References Cited

U.S. PATENT DOCUMENTS

| | | |
|---|---|---|
| 8,211,128 B1 | 7/2012 | Facundus et al. |
| 8,216,159 B1 | 7/2012 | Leiboff |
| 9,655,758 B2 | 5/2017 | Miesse et al. |
| 2003/0109916 A1 | 6/2003 | Don Michael |
| 2005/0059992 A1* | 3/2005 | Leiboff ................. A61M 31/00 606/197 |
| 2006/0129092 A1 | 6/2006 | Hanlon et al. |
| 2006/0217637 A1 | 9/2006 | Leiboff et al. |
| 2008/0249404 A1 | 10/2008 | Stokes et al. |
| 2010/0191265 A1 | 7/2010 | Lau et al. |
| 2011/0060192 A1 | 3/2011 | Pastron |
| 2012/0165604 A1 | 6/2012 | Mikkaichi et al. |
| 2013/0165774 A1 | 6/2013 | Nocca |
| 2014/0074014 A1 | 3/2014 | Branconier et al. |
| 2014/0114121 A1 | 4/2014 | Trivdei |
| 2014/0148731 A1 | 5/2014 | Radl et al. |
| 2014/0148732 A1* | 5/2014 | Radi .................... A61F 5/0089 600/593 |
| 2014/0236129 A1 | 8/2014 | Radl et al. |
| 2016/0136057 A1 | 5/2016 | Arif |
| 2016/0250056 A1 | 9/2016 | Keren et al. |

\* cited by examiner

METHOD FOR MAINTAINING SUCTION IN BODY CAVITIES

FIELD OF THE INVENTION

The present invention relates generally to gastric tubes, including nasogastric tubes and orogastric tubes, and more particularly to methods for maintaining suction in a body cavity using such tubes.

BACKGROUND OF THE INVENTION

Gastric tubes, either orogastric or nasogastric, have long been used to aspirate the stomach and to provide a means to introduce materials into the stomach, for example, nutrients, medicines or fluids used for testing, such as contrast for radiological imaging. They are passed through the nose or mouth, through the esophagus and into the stomach. They are particularly useful when the stomach or intestines are not functioning properly, for example during intestinal ileus or obstruction. However, they are often used routinely during certain abdominal surgeries, and at other times that require gastric decompression or feeding.

When gastric tubes are used to aspirate the stomach, negative pressure is delivered to the proximal end of the gastric tube. Negative pressure can be generated by a piston or bulb syringe. However, when suction is applied over an extended period of time, suction is usually achieved by attaching the tube via suction tubing to a collection canister which is in flow continuity with a suction regulator (usually located on a hospital room wall) which is connected to and modulates the negative pressure of the hospital's central suction source.

The amount of negative pressure applied to the gastric tube is variable. The ordering physician frequently requests "low suction", which is generally a range from 0 to 80 mmHg. However, treating personnel, such as nurses or other doctors, may apply higher levels of suction accidently, or purposely if the tube does not seem to be functioning, by dialing up the suction regulator.

Nasogastric and orogastric tubes are frequently used in abdominal surgery. The anesthesiologists and nurse anesthetists who manage the gastric tubes during surgery, often pay scant attention to the amount of negative pressure delivered to the stomach through the gastric tube. They employ high suction to the cannulas they use to aspirate the patient's mouth and upper airway, and frequently attach the suction tubing to the gastric tube without reducing the negative pressure.

High levels of suction can injure the gastric mucosa, the lining of the stomach. It would be advantageous to have a mechanism that more reliably prevents the application of high levels of suction to the stomach and gastric wall. It would also be advantageous to have a mechanism that alerts the doctors, nurses and other caregivers that the suction pressure may be excessive.

Gastric operations have been increasing in frequency due to the increasing popularity of bariatric or "weight loss" surgery. These operations use gastric tubes, usually orogastric tubes, to aspirate and decompress the stomach in order to facilitate surgery on the organ. Gastric tubes may also facilitate the surgery by providing a guide or gauge to help size the residual stomach. Bougies, solid flexible cylinders, inserted into the stomach through the mouth and esophagus, have been used as a guide or gauge to size the residual stomach. However gastric tubes are advantageous because they may serve the same purpose without requiring the passage of a second instrument to aspirate and decompress the stomach.

Sleeve gastrectomy is an operation wherein a portion of the stomach is removed in a longitudinal fashion so as to create a stomach that is narrow and more tubular. It has been found useful to divide and staple closed the stomach while a large caliber gastric tube is in place within the remaining portion of the stomach. Suction applied to the stomach through the tube serves to decompress the stomach and stabilize it while stapling and cutting is performed. To improve the decompressing and stabilizing functions of the tube, the distal portions of the tube that are situated within the stomach are provided with multiple apertures.

Applying suction through a large caliber tube with multiple apertures may expose the lining of the stomach to injury. It is therefore important to have a reliable means to regulate the negative pressure delivered to the stomach during these operations. US Patent Application Publication No.: US 2014/0236129 A1 describes an integrated suction controller that limits the amount of negative pressure that can be delivered to the stomach. However, this suction controller has disadvantages. It is relatively bulky and it is situated in line which could interfere with suction when particulate debris or blood clots accumulate in the suction regulator and obstruct flow.

It would therefore be advantageous to have a gastric tube that is capable of reliably limiting the degree of suction delivered to the stomach or distal end of the tube, independent of the setting of the suction regulator modulating the pressure from the suction source, that achieves this through a simple, small, lightweight, inexpensive mechanism, integral with the tube, that cannot obstruct flow through the tube. As an additional safeguard, it would also be advantageous if such a mechanism produced a signal when excessive suction is applied to the tube.

Gastric tubes used in gastric surgery serve functions other than aspiration. They may be useful as sizers or templates that help the surgeon configure a gastric tube or pouch, as in sleeve gastrectomy. Or they may incorporate an inflatable cuff (balloon) at its distal end, as described in U.S. Pat. No. 8,211,128, to help size the gastric pouch in gastric bypass surgery.

Gastric tubes may also serve as a conduit for instilling a dye, such as methylene blue, into the stomach as a means to test the integrity of the sutured or stapled closure. Defects in the suture or staple line are identified when dye leaks out of the stomach.

A convenient means to instill dye into the stomach using the gastric tube as a conduit would be advantageous.

Gastric tubes may also function as a conduit to inflate the residual stomach with air as an alternate means to test the integrity of the sutured or stapled closure. This technique involves inflating the stomach with air while the suture line or staple line is submerged in saline. Bubbles seen in the fluid pool around a closure while the stomach is inflated indicate there is a leak, or defect in the closure, which then must be identified and repaired. It has been found that it is important to control the specific air pressure within the stomach when testing the gastric suture line with air.

Incorporation into a gastric tube or gastric tube system of convenient means to inflate the residual stomach with air and to monitor the positive air pressure in the stomach during inflation would also be advantageous.

Means to inflate the stomach and monitor the gastric pressure exist. U.S. Pat. No. 8,211,128 describes an inflator bulb useful for inflation and an attached manometer or pop-up indicator that are useful form monitoring gastric pressure. A stand alone device, the Bariatric Anastomosis Leak Tester, Tools for Surgery, LLC, is available for attachment to an appropriate gastric tube for these purposes.

SUMMARY OF THE INVENTION

A gastric tube in accordance with one or more embodiments of the invention includes a tube having an elongate distal portion with at least one lumen and at least one aperture at or in proximity to its distal end, a proximal portion having at least two arms, each arm comprising a lumen in flow communication with the lumen of the other arm of the proximal portion and with the lumen of the elongate distal portion, one arm having an opening adaptable to communicate with a suction source or to a syringe for instilling a dye solution into the body cavity or to an inflation device for inflating with air the body cavity containing the distal end of the tube. The second arm comprises means to control or monitor, or control and monitor negative pressure within the lumens of the tube and body cavity, e.g., a valve or indicator valve.

Using such a tube, a method for introducing and maintaining a level of negative pressure in a body cavity of at least 80 mmHg in accordance with the invention includes inserting the elongate distal portion of a gastric tube into the body cavity, coupling a proximal end of the first arm via tubing to a suction source, and applying, after the distal portion of the tube is inserted into the body cavity and the proximal end of the first arm is coupled to the suction source, negative pressure from the suction source to the body cavity through the distal portion and maintaining an intraluminal negative pressure in the tube of at least 80 mmHg. The valve is configured to enable intraluminal negative pressure to be maintained in the tube at at least 80 mmHg, possibly even greater than a value in a range from 100 mmHg to about 150 mmHg, and such that while the intraluminal negative pressure in the tube is maintained at at least 80 mmHg or higher, two conditions are satisfied, namely, the valve does not allow passage of air therethrough when ambient air pressure exceeds air pressure within the lumens of the tube until a difference between the ambient air pressure and the intraluminal negative pressure exceeds a specified amount associated with the valve that is greater than 80 mmHg or higher, and the difference between the ambient air pressure and the intraluminal negative pressure exceeding the specified amount causes the valve to change from a closed state in which ambient air is prevented from flowing through the valve into the lumens of the tube to an open state in which the valve allows ambient air to flow through the valve into the lumens of the tube in order to limit the intraluminal negative pressure and the negative pressure within the body cavity to a pressure within a desirable range. A negative pressure "higher" or "greater" than 80 mmHg value means greater negative pressure, i.e., 100 mmHg negative pressure is higher or greater than 80 mmHg negative pressure.

Other embodiments of tubes that may be used in the method include an embodiment that provides means to reduce pressure within the lumens of the tube, which may be the valve mention above. The valve is disposed in relation to the second arm opens and ambient air flows through the valve when negative air pressure within the tube exceeds a reference pressure. This serves to reduce (make less negative) the negative pressure within the lumen of the elongate portion of the tube and within the body cavity in communication with the lumen of the elongate tube through the aperture or apertures at the distal end of the tube.

A gastric tube in accordance with a second embodiment of the invention comprises means disposed in relation to the second arm that provide an audible signal when negative air pressure within the tube exceeds a reference pressure.

A gastric tube in accordance with a third embodiment comprises means disposed in relation to the second arm that provide a visual signal when negative air pressure within the lumens of the tube exceeds a reference pressure.

A gastric tube in accordance with a fourth embodiment of the invention comprises means disposed in relation to the second arm that reduce pressure within the lumens of the tube and produce an audible signal when negative air pressure within the tube exceeds a reference pressure. A valve disposed in relation to the second arm opens and ambient air flows through the valve when negative air pressure within the tube exceeds a reference pressure. This serves to reduce the negative pressure within the lumen of the elongate portion of the tube and within the body cavity in communication with the lumen of the elongate tube through the aperture or apertures at the distal end of the tube. When air flows through the valve at a certain rate, an audible signal is produced as a result of vibration of elements of the valve.

A gastric tube in accordance with a fifth embodiment of the invention comprises means disposed in relation to the second arm that reduce pressure within the lumens of the tube and produce a visual signal when negative air pressure within the tube exceeds a reference pressure. A valve disposed in relation to the second arm opens and ambient air flows through the valve when negative air pressure within the tube exceeds a reference pressure. This serves to reduce the negative pressure within the lumen of the elongate portion of the tube and within the body cavity in communication with the lumen of the elongate tube through the aperture or apertures at the distal end of the tube. When the valve opens an element of the valve or an associated indicator visibly moves and provides a visual signal that the negative pressure within the tube has exceeded the reference pressure.

In methods of sizing a gastric sleeve in gastric surgery in accordance with the invention, any of the disclosed embodiments of the tube is inserted so that a segment of the elongate distal portion of the tube is situated in the stomach in a desired location in the stomach, generally along the lesser curvature, and the stomach is placed on suction through the tube so that the tube is fixed in location and delineates the optimal location for a resection and closure line. Excessive negative pressure on the wall of the stomach is prevented by the presence of a pressure relief valve or by an auditory and/or visual indicator arranged in relation to the second arm of the tube that signals that the negative pressure transmitted to the stomach is excessive so that the operating room personal, generally the anesthesiologist or a nurse, can act to reduce the suction pressure by manipulating a suction pressure regulator.

A gastric tube in accordance with a sixth embodiment comprising the features of one of the first five embodiments, and wherein the distal portion comprises two lumens, the second lumen having an aperture proximal to the distal end of the tube that is in flow communication with an inflatable cuff, the second lumen being in flow communication with the lumen of a third arm of the proximal portion of the tube, the third arm lumen being in flow communication with the interior of a valve through which air or fluid may be injected to inflate the inflatable cuff.

In a method of sizing a gastric pouch in gastric surgery in accordance with the invention, a portion of the elongate distal portion of the sixth embodiment of the gastric tube is inserted into the stomach, the stomach is decompressed by applying suction to the first arm of said tube, the inflatable cuff is inflated by injecting air through a valve in flow communication with a second lumen of said tube that is in flow communication with the cuff by means of an aperture in the tube, and the inflatable cuff is used as a template or sizer for the surgeon to gauge the size of the pouch.

BRIEF DESCRIPTION OF THE DRAWINGS

The invention, together with further objects and advantages thereof, may best be understood by reference to the following description taken in conjunction with the accompanying drawings wherein like reference numerals identify like elements.

DETAILED DESCRIPTION OF THE INVENTION

Figure 1:
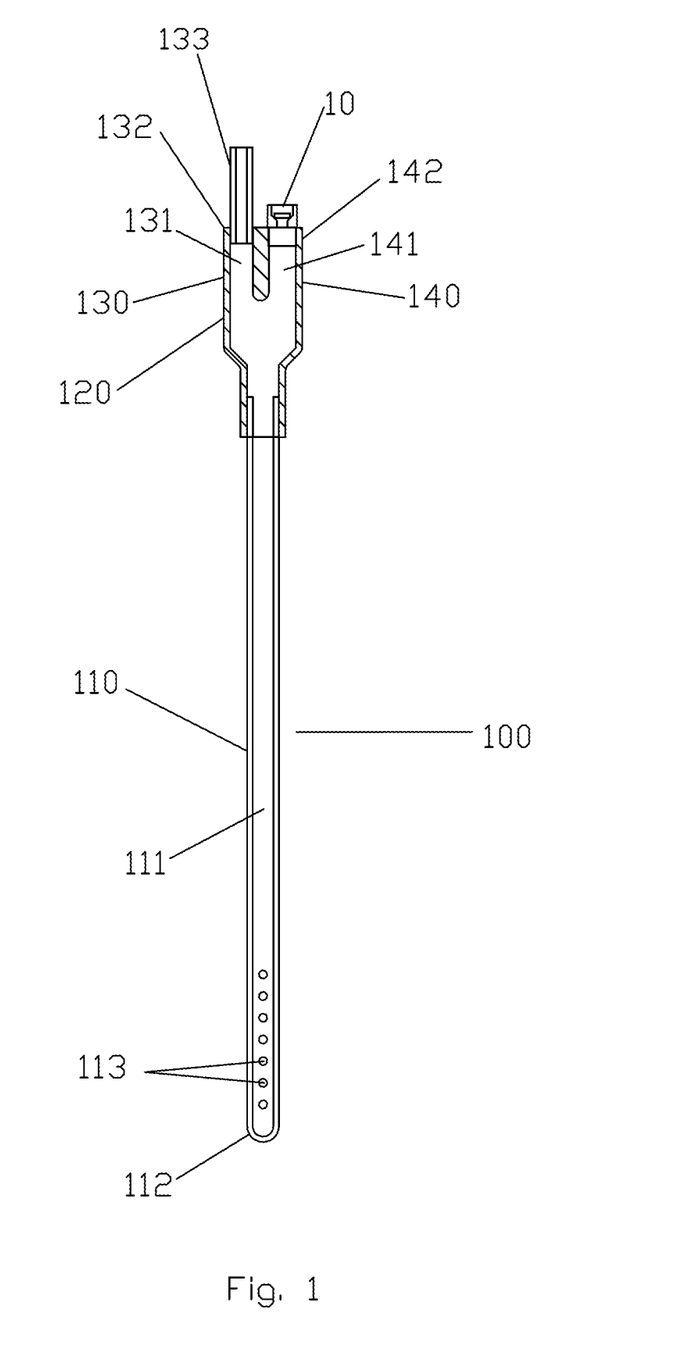
FIG. 1 is a diagrammatic view of a first embodiment of a tube insertable into a body cavity in accordance with the invention that reduces negative pressure within its lumens when negative pressure exceeds a specified pressure.

Referring now to FIG. 1, a first embodiment of a tube for insertion into a body cavity, or more specifically, a gastric tube, according to the invention is designated generally as 100 and includes elongate distal portion 110 and proximal portion 120. Distal portion 110 comprises lumen 111 and at least one aperture 113 in proximity to distal end 112. Proximal portion 120 has two arms, first arm 130 and second arm 140, which may be alongside one another as shown. First arm 130 comprises lumen 131 and proximal end 132. End 132, or extension 133, is adaptable to a tubing from a suction source (not shown). Second arm 140 has lumen 141 and end 142. Lumens 111, 131 and 141 are always in flow communication. Extension 133 is tubular and extends from the end 132, and both the end 132 and the extension 133 may be adaptable to tubing from the suction source. Proximal portion 120 may be formed integral with the distal portion 110 or separate therefrom and then attached securely thereto. Distal portion 110 may be made of one or more elastomeric materials and is preferably flexible.

End 142 is adaptable to valve 10. This means that the valve 10 may be partly received in the lumen 141 and extend partly out of the end 142, that the valve 10 is attached to the end 142 so that it is only situated exterior of the second arm 140, or that the valve 10 is entirely within an area proximate the end 142 of the second arm 140. As shown, the valve 10 is at one end region of the lumen 141 with the other end region being open to a common space in the distal portion 120 to which the lumen 131 also opens. Mating or engagement structure to enable the valve 10 to be secured to the end 142 is provided, whether entirely on the valve 10, entirely at or on the end 142 or partly on the valve 10 and the end 142.

Valve 10 is a pressure relief valve that opens when the pressure differential between the air in lumen 141 and ambient air exceeds a specified quantity, thus allowing ambient air to flow into lumen 141 and reduce the negative air pressure in lumens 141, 131 and 111. The negative air pressure in the lumens 111, 131, 141 is referred to as the intraluminal pressure. The specified quantity may be determined by the manufacturer for various operational situations and an appropriate valve selected accordingly dependent on, for example, the use of the tube 100. For example, valve 10 may be one of many commercially available valves, including Halkey Roberts part number 730ROAR25, which will open only when the air pressure differential exceeds 129 mmHg. The degree of air pressure reduction will partly depend on the relative air flow in lumens 131 and 141, which depends upon several factors, including the flow capacity of the suction source, and the cross-sectional flow area of valve 10.

In a preferred embodiment, the air pressure differential that automatically causes opening the valve 10 is at least 80 mmHg. This is a cause and effect relationship whereby ambient air pressure exceeding air pressure within the lumens 111, 131, 141 of the tube 100 by the specified amount (e.g., at least 80 mmHg) automatically causes the valve 10 to change from a closed state in which ambient air is prevented from flowing through the valve 10 into the lumens 111, 131, 141 of the tube 100 to an open state in which the valve 10 allows ambient air to flow through the valve 10 into the lumens 111, 131, 141 of the tube 100 in order to reduce air pressure within the lumens 111, 131, 141 of the tube 100 and within the body cavity which is in flow communication with the lumens 111, 131, 141 of the tube 100. The reduction of air pressure is a lower absolute value of the negative pressure prevailing in the lumens 111, 131, 141 of the tube 100, all of which are in continual flow communication with one another regardless of the state of the valve 10, i.e., in both the open and closed states of the valve 10 (i.e., the intraluminal pressure prevails throughout the lumens 111, 131, 141).

This cause and effect relationship governing automatic opening of the valve 10 depending on the ambient air pressure exceeding air pressure within the lumens 111, 131, 141 of the tube 100 by the specified amount means that if the air pressure within the lumens 111, 131, 141 is such that if the ambient air pressure does not exceed it by the specified amount, the valve 10 does not open and remains in the closed state preventing ambient air from flowing into the lumens 111, 131, 141. This allows for build-up of a desired level of negative pressure in the body cavity, e.g., there may be a prevailing negative pressure in the body cavity of at least 80 mmHg, maybe even 119 mmHg. The negative pressure may be in a range greater than 100 mmHg.

By automatic opening of the valve 10, it is meant that manual intervention, interference or handling of the valve 10 by an operator is not required. Rather, the valve 10 is configured to inherently and automatically respond to the relative pressure (relative pressure difference between ambient air pressure and pressure in the lumens 111, 131, 141 of the tube 100) equaling or exceeding the specified amount that is obtained through design of the tube 100 and selection of the valve 10 therein.

The invention also comprises a method wherein a distal segment of the elongate distal portion 110 of the first embodiment of a gastric tube is inserted through a patient's nose or mouth, through the pharynx and esophagus into the patient's stomach. Extension 133 is attached to tubing from a suction source (not shown). If the negative pressure within lumen 141 exceeds a specified negative pressure, valve 10 will open and ambient air will flow into tube 100 to reduce the negative pressure within tube 100 and the negative pressure within the stomach, which is in flow continuity with lumens 111,131 and 141 through a single or plurality of apertures 113.

In this manner, it becomes possible to control the level of negative pressure in the tube 100 since if the negative pressure in the tube 100 were to be present at a value (120 mmHg) such that the ambient air pressure exceeds this negative pressure by a specified amount determined by the selection and construction of the valve (119 mmHg), then the valve 10 would open automatically. Excessive negative pressure in the tube 100 and thus in the body cavity is prevented from occurring, thereby preventing damage to the body cavity. The tube 10 thus imposes a limit on the negative pressure in the body cavity and is useful in the event, for example, the suction administrator is inattentive and is not focusing on the application of the negative pressure to the body cavity through the tube 100.

Figure 2:
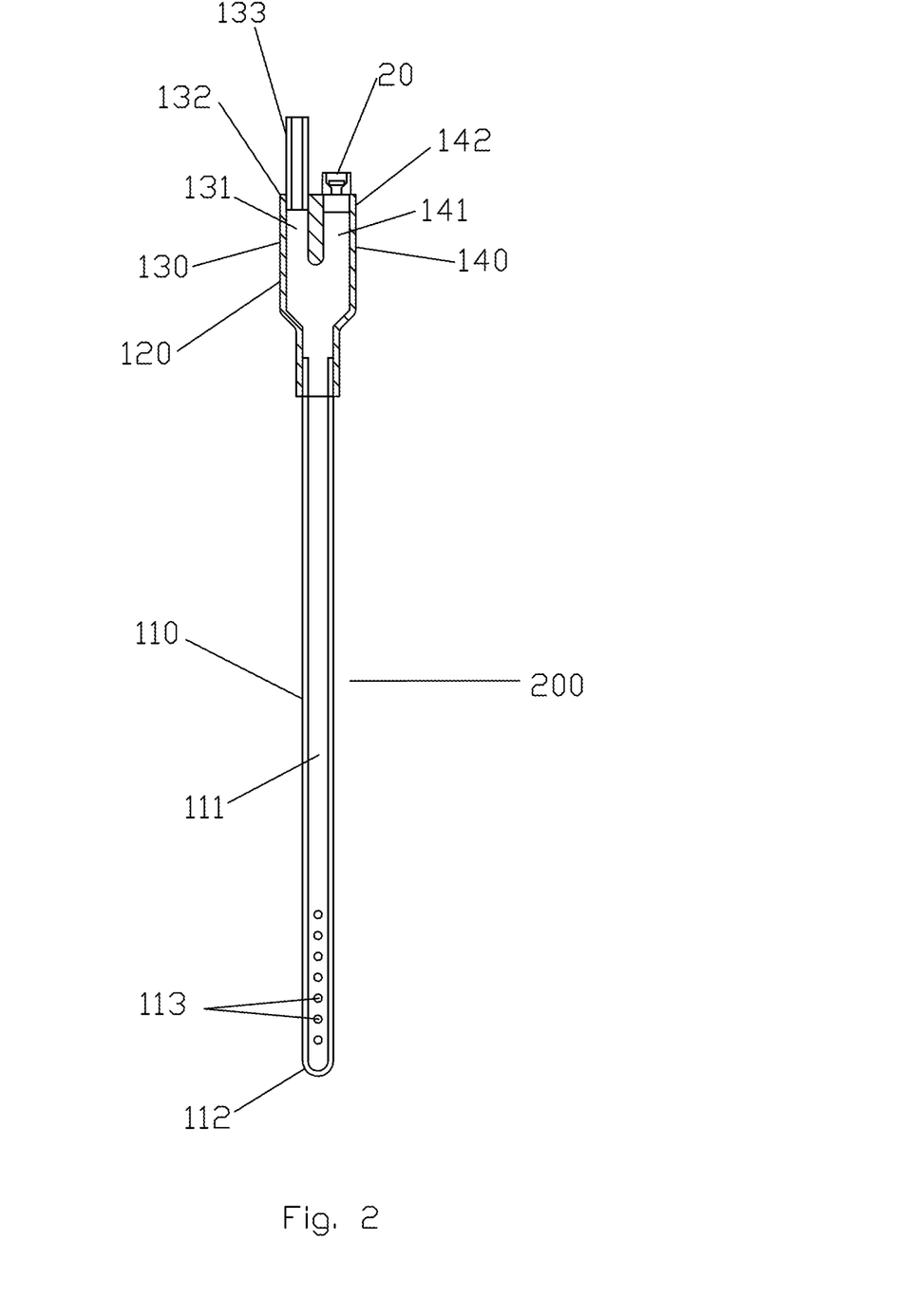
FIG. 2 is a diagrammatic view of a second embodiment of a tube insertable into a body cavity in accordance with the invention that provides an audible signal when negative pressure within its lumens exceeds a specified pressure.

Referring now to FIG. 2, a second embodiment 200 of a gastric tube comprises features of the first embodiment and additional features (and the same reference numbers designate the same parts as in the first embodiment described above). Second arm 140 of tube 200 comprises lumen 141 and end 142 adaptable to indicator 20 in a similar manner that valve 10 is adaptable to the end 142. Indicator 20 emits an audible signal when air flow through it exceeds a specific velocity. Halkey Roberts part number 730ROAR25 is one such indicator. Indicator 20 also comprises a valve that reacts to a pressure differential above a specified amount, e.g., 80 mmHg, like valve 10

Selection of an indicator 20 that is capable of emitting an audible signal itself when air flow through it exceeds a specific velocity, and not emitting the audible signal when the air flow through it does not exceed the specified velocity is an important aspect of the invention since the intrinsic structure of the indicator 20 (or valve) is used to generate the audible signal. In this embodiment, the indicator 20 may be in an open position, but no audible signal is generated based on this open position since the velocity of the air flow through the indicator 20 does not exceed the specified velocity. Only when the velocity of the air flow through the indicator 20 exceeds the specified velocity is the audible signal generated by the indicator 20 itself. The audible signal is not generated whenever the indicator 20 is open, but only when the indicator 20 is open and the velocity of air flow therethrough exceeds the specified velocity (satisfying both conditions). Such embodiments lack, among other things, an additional controller to measure pressure and generate a signal.

Indeed, in other tubes, there is an additional mechanism such as flaps or the like that is placed into the flow path in order to react to the flow exceeding a set velocity and then generate an audible signal. Rather, the audible signal is produced by, for example, vibration of elements of the indicator 20, without the need for additional structure. By eliminating an additional mechanism, the embodiments of the invention including the audible signal-generating indicator or valve provide for significant advantages not previously realized nor believed to be obvious to those skilled in the art to which this invention pertains.

Figure 3:
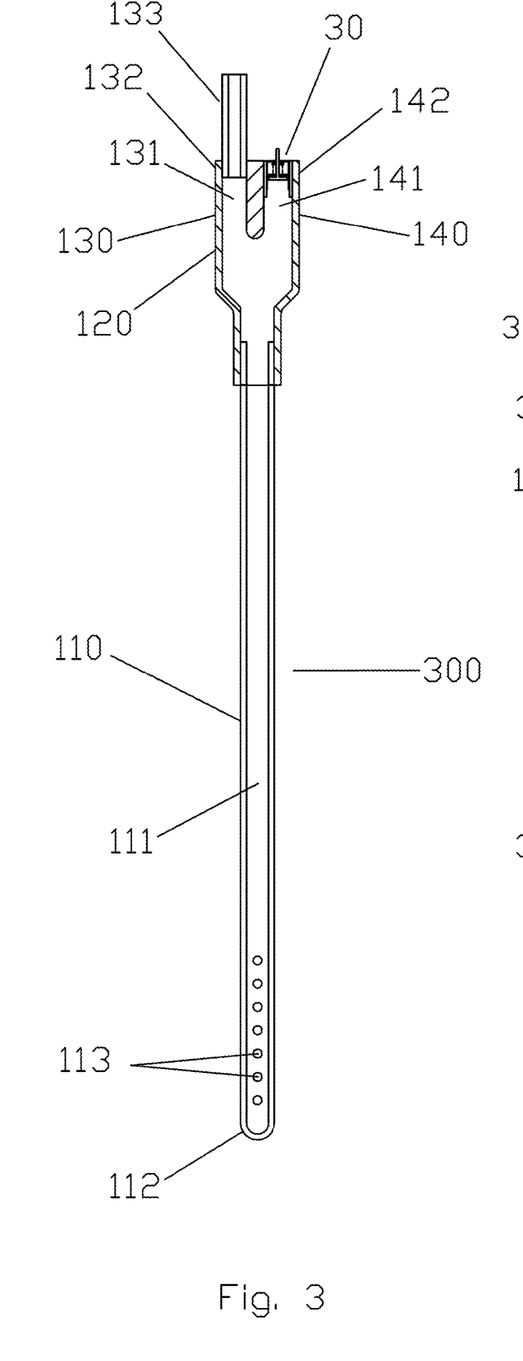
FIG. 3 is a diagrammatic view of a third embodiment of a tube insertable into a body cavity in accordance with the invention that provides a visual signal when negative pressure within its lumens exceeds a specified pressure.
Figure 3A:
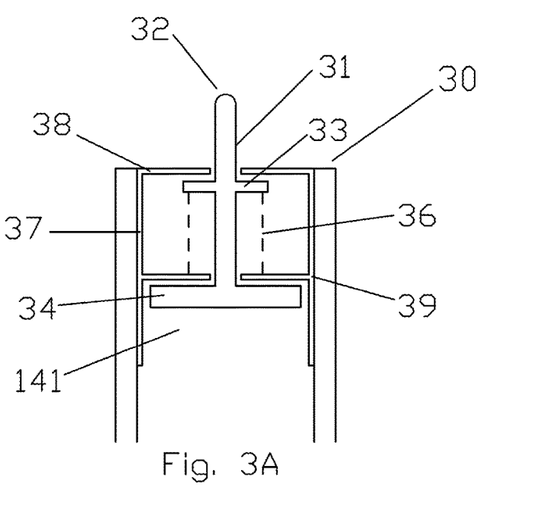
FIG. 3A is a cross sectional view of a second arm of the third embodiment comprising a lumen and indicator in a non-actuated posture.
Figure 3B:
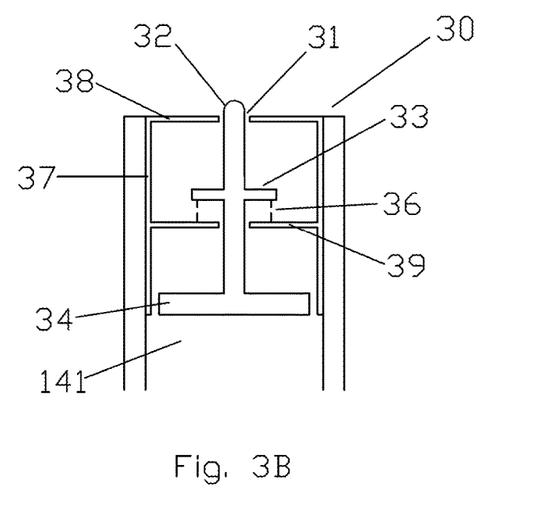
FIG. 3B is a cross sectional view of a second arm of the third embodiment comprising a lumen and indicator in an actuated posture.

Referring now to FIGS. 3, 3A and 3B, a third embodiment 300 of a gastric tube in accordance with the invention comprises features of the first embodiment and additional features (and the same reference numbers designate the same parts as in the first embodiment described above). Second arm 140 of tube 300 comprises lumen 141 and end 142 adaptable to indicator 30, in a similar manner as valve 10 is adaptable to the end 142. Indicator 30 comprises housing 37 arranged entirely in the lumen 141 and piston 31 arranged in housing 37. FIGS. 3 and 3A show indicator 30 in a non-actuated posture. FIG. 3B shows indicator 30 in an actuated posture. Spring 36 in the interior of the housing 37 biases diaphragm 33 of piston 31 towards a top 38 of housing 37. When negative pressure in lumen 141 of arm 140 exceeds a specified pressure, determined by, for example, the mechanical properties of spring 36 of indicator 30, head 34 of piston 31 is drawn inward and away from diaphragm 39 of housing 37. End 32 of piston 31 moves toward top 38 of housing 37 (downward in FIGS. 3A and 3B), shortening the exposed portion of piston 31, with this movement providing a visual signal that the negative pressure within lumens 141, 131 and 111 exceeds a specified pressure. Ambient air is then able to flow around the piston 31 through the top 38 of the housing and the diaphragm 39 into the lumen 141.

Figure 4:
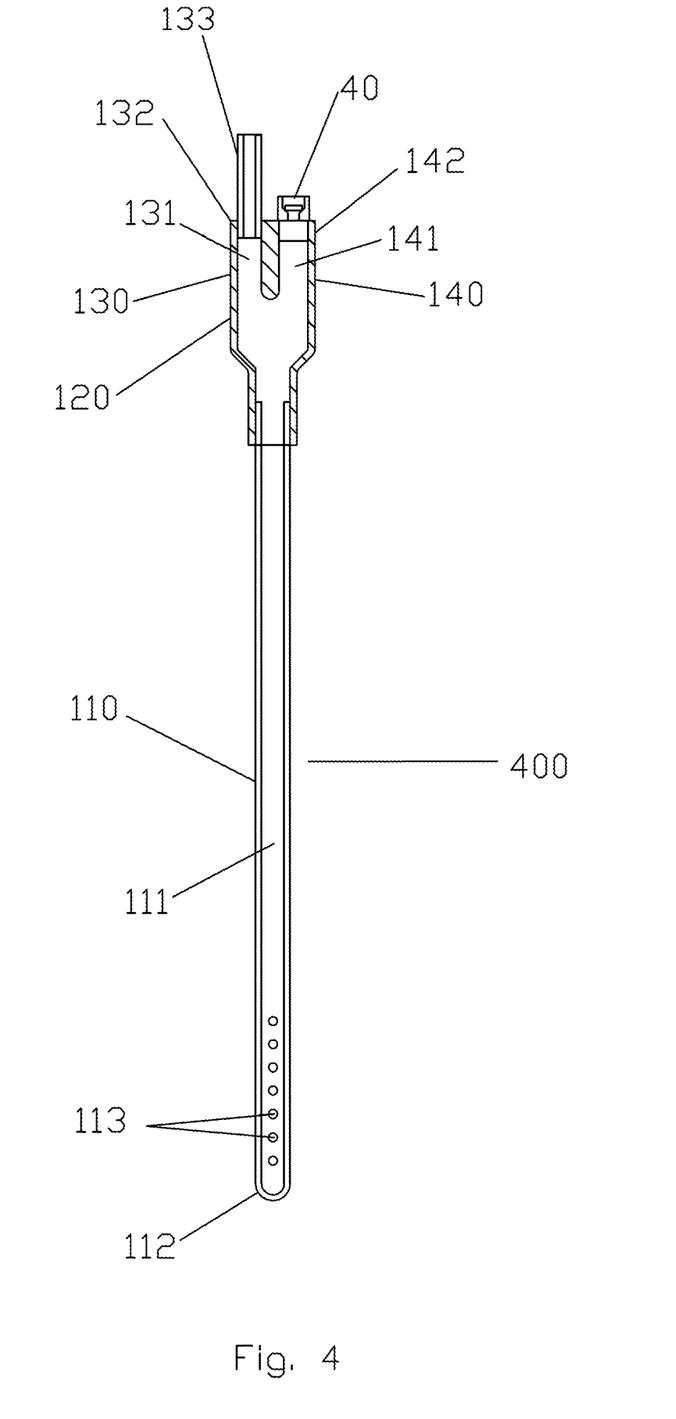
FIG. 4 is a diagrammatic view of a fourth embodiment of a tube insertable into a body cavity in accordance with the invention that reduces negative pressure within its lumens when negative pressure exceeds a specified pressure and provides an audible signal when negative pressure within its lumens exceeds a specified pressure.

Referring now to FIG. 4, a fourth embodiment 400 of a gastric tube in accordance with the invention comprises features of the first embodiment and additional features (and the same reference numbers designate the same parts as in the first embodiment described above). Second arm 140 of tube 400 comprises lumen 141 and end 142 adaptable to indicator valve 40 in a similar manner as valve 10 is adaptable to the end 142. Indicator valve 40 is configured to open when the pressure differential between the air in lumen 141 and ambient air exceeds a specified quantity, e.g., 80 or 100 mmHg, thus allowing ambient air to flow into lumen 141 and reduce the negative air pressure in lumens 141, 131 and 111. The specified quantity may be determined by the manufacturer for various operational situations and an appropriate indicator valve selected accordingly. Indicator valve 40 also provides an audible signal when air flow through the indicator valve 40 exceeds a specified velocity. The specified velocity may be determined by the manufacturer for various operational situations and an appropriate indicator valve selected accordingly. For example, indicator valve 40 may be one of many commercially available valves, including Halkey Roberts part number 730ROAR25, which opens when the air pressure differential exceeds 129 mmHg and which emits an audible signal when air flow through it exceeds a specific velocity.

Figure 5:
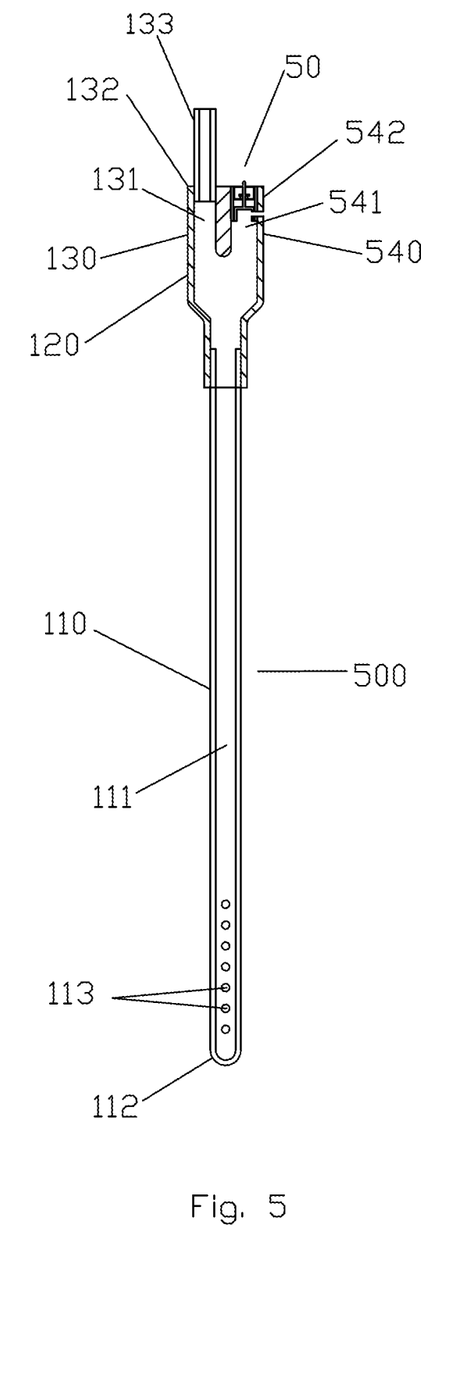
FIG. 5 is a diagrammatic view of a fifth embodiment of a tube insertable into a body cavity in accordance with the invention that reduces negative pressure within its lumens when negative pressure exceeds a specified pressure and provides a visual signal when negative pressure within its lumens exceeds a specified pressure.
Figure 5A:
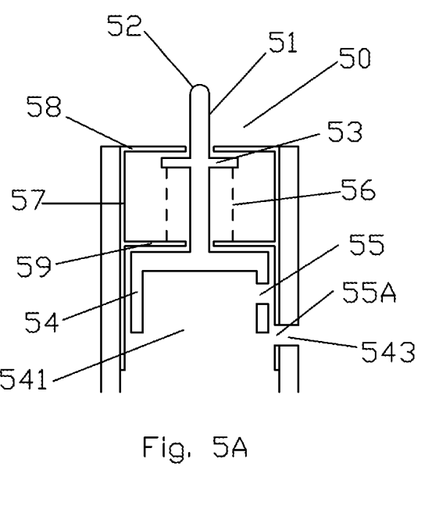
FIG. 5A is a cross sectional view of a second arm of the fifth embodiment comprising a lumen and indicator valve in a non-actuated posture.
Figure 5B:
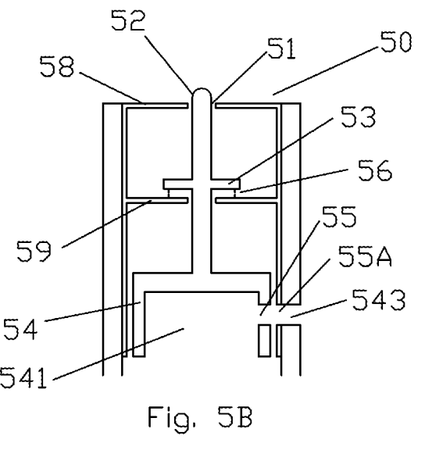
FIG. 5B is a cross sectional view of a second arm of the fifth embodiment comprising a lumen and indicator valve in an actuated posture.

Referring now to FIGS. 5, 5A and 5B, a fifth embodiment 500 of a gastric tube in accordance with the invention comprises features of the first embodiment and additional features (and the same reference numbers designate the same parts as in the first embodiment described above). Second arm 540 of tube 500 comprises lumen 541 and end 542 adaptable to indicator valve 50 in a similar manner as valve 10 is adaptable to the end 142. Indicator valve 50 comprises housing 57 arranged entirely in the lumen 541 and piston 51 arranged in housing 57. FIGS. 5 and 5B show indicator valve 50 in an actuated posture. FIG. 5A shows indicator valve 50 in a non-actuated posture. Spring 56 in the interior of the housing 57 biases diaphragm 53 of piston 51 towards a top 58 of housing 57. When negative pressure in lumen 541 of arm 540 exceeds a specified pressure as determined by, for example, the mechanical properties of spring 56, cylindrical portion 54 of piston 52 is drawn inward and away from diaphragm 59 of housing 57. End 52 of piston 51 moves toward the top 58 of housing 57, shortening the exposed portion of piston 51, with this movement providing a visual signal that the negative pressure within lumens 541, 131 and 111 exceeds a specified pressure.

Housing 57 comprises at least one aperture 55A in a portion situated alongside a peripheral wall of arm 540. When cylindrical portion 54 of piston 51 moves inward, the at least one slotted aperture 55 of cylindrical portion 54 of piston 51 moves into alignment with at least one aperture 55A of housing 57 and at least one aperture 543 of second arm 540 of tube 500, thereby allowing ambient air to enter interior of cylindrical portion 54 and flow into lumen 541 of arm 540 thereby reducing pressure in lumen 540 and lumen 111 of elongate portion 110 of tube 500 and in the body cavity.

Figure 6:
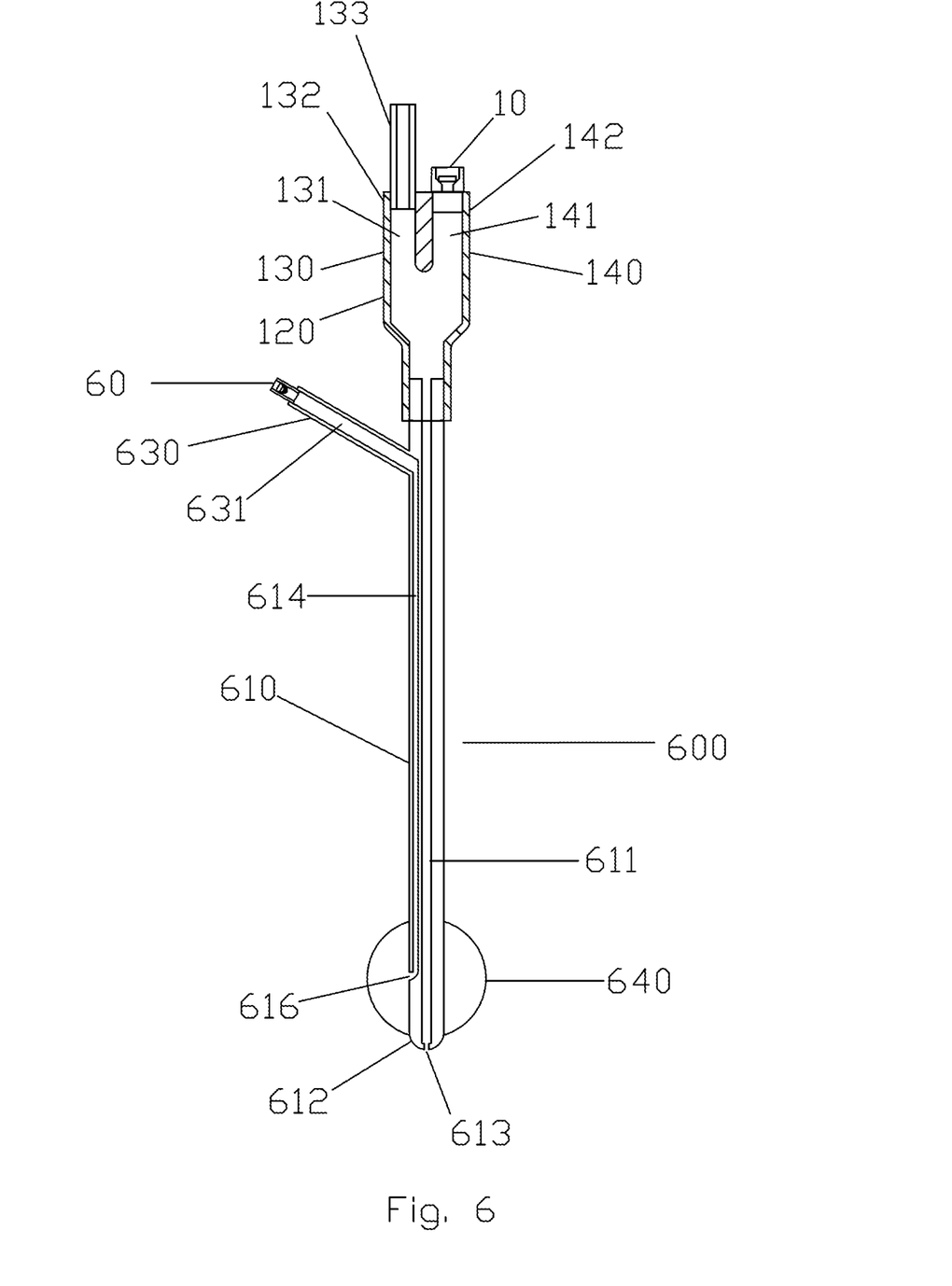
FIG. 6 is a diagrammatic view of a sixth embodiment of a tube insertable into a body cavity in accordance with the invention that reduces negative pressure within its lumens when negative pressure exceeds a specified pressure and provides an audible signal when negative pressure within its lumens exceeds a specified pressure and provides an inflatable cuff to size a gastric pouch.

Referring now to FIG. 6, a sixth embodiment 600 of a gastric tube in accordance with the invention comprises the features of the first embodiment and additional features (and the same reference numbers designate the same parts as in the first embodiment described above). Elongate distal portion 610 of tube 600 comprises a second lumen 614, which has aperture 616 so that lumen 614 is in flow communication with the interior of inflatable cuff 640. Inflatable cuff 640 comprises an elastomeric sheath that inflates when air is forced into its interior. Lumen 614 is in flow communication with lumen 631 of arm 630, arm 630 being situated at or in proximity to the proximal end of elongate portion 610. Valve 60, located at proximal end of arm 630, communicates with lumen 631 of arm 630. Valve 60 may be a commercially available valve. When a syringe is inserted into valve 60, air may be injected into lumen 631 of arm 630, or withdrawn from lumen 631. The inflatable cuff 640 can thereby be inflated and deflated. Inflatable cuff 640 may serve as a template or sizer for the surgeon to gauge the size of the gastric pouch that he creates in gastric bypass surgery.

The invention also comprises a method of sizing a gastric pouch in gastric surgery, whereby a portion of the elongate distal portion 610 of a sixth embodiment 600 of the gastric tube is inserted into a stomach, the stomach decompressed by applying suction to the first arm 130 of the tube, the inflatable cuff 640 inflated by injecting air through valve 60 that is in flow communication with second lumen 614 and inflatable cuff 640, by means of aperture 616, causing inflatable cuff 640 to inflate. The inflated cuff is used as a template or sizer for the surgeon to gauge the size of a gastric pouch.

Embodiments of the present invention provide advantages over prior art tubes, for example, a tube including a valve disclosed in Radl et al. (US 20140148732).

The valve in Radl et al. is a slide valve that includes a body having a first coupling which is tubular and arranged to be disposed (e.g., frictionally fit) within a hollow proximal end of a sizing tube. The body includes a second coupling which is also a tubular member, the couplings are axially aligned with each other and project radially outward from diametrically opposed locations on the body of the valve, and the body is a hollow member in which a slide is disposed (see FIG. 2). The slide is arranged to be slid into one of two positions to cause the valve to be in either an open ("on") position (FIG. 2) or a closed ("off") position (FIG. 1). The slide is a hollow tubular member having a first end cap or head at one end thereof and a second end cap or head at the opposite end thereof and a pair of diametrically aligned openings located in the side wall of the slide half way between the heads. When the slide is in the open position shown in FIG. 2, the openings in the slide are aligned with the hollow interior of couplings thereby providing a fluid path therethrough. When the slide is in the closed position shown in FIG. 1, the openings in the slide are not aligned with the hollow interior of the couplings, so that the side wall of the slide blocks the interior of the two couplings, thereby isolating the couplings from each other.

As such, when the valve is in the "open (on)" position shown in FIG. 2, there is no flow communication between the lumen of the tube with ambient air. On the other hand, when the valve is in the "closed (off)" position shown in FIG. 1, there is flow communication between the lumen of the tube and ambient air. However, in this closed position where there is direct communication between ambient air and the lumen of the tube, there is no intervening structure that can prevent the flow of ambient air into the tube when the difference in pressure between ambient air and the tube does not exceed a specified amount. Since there is direct, unregulated communication in this closed valve position, ambient air will flow into the lumen as soon as negative pressure is applied to the lumen.

In contrast to the claimed invention, the valve in Radl et al. is therefore configured so that when it is in the closed position, and ambient air pressure exceeds air pressure within the lumens of the tube by any amount, the valve allows flow of ambient air into the lumens of the tube to reduce air pressure. The construction of the valve does not allow the inflow of air into the tube to be limited to a specified difference between intraluminal and ambient pressures, other than the condition that ambient air pressure exceeds intraluminal pressure. Furthermore, in this closed position, suction cannot be delivered to tube because the luminal pathway to the suction apparatus is blocked.

Another important aspect of the invention is that the valve 10, and other indicators and valves, open when ambient air pressure (atmospheric pressure) exceeds gastric pressure (essentially the same as the intraluminal pressure) by a specified amount of at least 80 mmHg which allows for a negative pressure to prevail in the body cavity. Prior art gastric tubes do not include a mechanism that enables a gastric pressure greater than negative 80 mmHg, and specifically between negative 100 to 150 mmHg. To this end, valves used in the invention that include a spring, e.g., valves 30, 50, can be designed so that the spring that will not allow the valve to open until atmospheric pressure exceeds gastric pressure by at least more than 100 mmHg, and this opening allows air flow into the gastric tube. By contrast, prior art tubes open based on any difference between the atmospheric pressure and the pressure in a body cavity or a nominal pressure difference, and moreover, often provide for air flow from the gastric tube to the ambient atmosphere, i.e., to relieve overpressurization, or prevent reflux of fluid. These prior art tubes do not envision an embodiment wherein it is desirable to maintain negative pressure in the gastric tube and body cavity at a level of at least 80 mmHg and often in a range from about 100 to about 150 mmHg.

The pressure values, and other dimensions, mentioned herein may be approximate values, e.g., a pressure of 80 mmHg should be considered about 80 mmHg. The extent to which the identified physical property may be above or below the recited value would be understood by those skilled in the art to which this invention pertains.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention. Also, various features of the specific embodiments described above may be used in other described embodiments.

The invention claimed is:

1. A method for introducing and maintaining a level of negative pressure in a patient's body cavity of at least 80 mmHg, the method comprising:
    inserting an elongate distal portion of a gastric tube into the body cavity, the distal portion comprising a lumen and at least one aperture in proximity to a distal end, the tube including a proximal portion having
        a first arm comprising a lumen,
        a second arm comprising a lumen, and
        a common space in flow communication with the lumen of the distal portion and the lumens of the first and second arms and interposed between the lumens of the first and second arms and the lumen of the distal portion such that any flow from the lumens of the first and second arms to the lumen of the distal portion flows through the common space and any flow from the lumen of the distal portion to the lumens of the first and second arms flows through the common space, and the tube further including a valve arrangeable relative to the second arm;
    coupling a proximal end of the first arm via tubing to a suction source; and
    applying, after the distal portion of the tube is inserted into the body cavity and the proximal end of the first arm is coupled to the suction source, negative pressure from the suction source to the body cavity through the lumen of the first arm, through the common space and through the lumen of distal portion and maintaining an intraluminal negative pressure in the tube of at least 80 mmHg,
    the valve being configured to enable intraluminal negative pressure to be maintained in the tube at at least 80 mmHg and such that while the intraluminal negative pressure in the tube is maintained at at least 80 mmHg:
        the valve does not allow passage of air therethrough when ambient air pressure exceeds air pressure within the lumens of the tube until a difference between the ambient air pressure and the intraluminal negative pressure exceeds a specified amount associated with the valve that is greater than 80 mmHg, and
        the difference between the ambient air pressure and the intraluminal negative pressure exceeding the specified amount causes the valve to change from a closed state in which ambient air is prevented from flowing through the valve into the lumens of the tube to an open state in which the valve allows ambient air to flow through the valve into the lumen of the second arm through the common space and into the lumen of the distal portion in order to limit the intraluminal negative pressure and the negative pressure within the body cavity to a pressure within a desirable range.

2. The method of claim 1, wherein the step of inserting the elongate distal portion of the tube into the body cavity comprises inserting the elongate distal portion through the patient's nose or mouth, through the patient's pharynx and esophagus into the patient's stomach.

3. The method of claim 2, further comprising placing a segment of the elongate distal portion of the tube along the lesser curvature of the patient's stomach.

4. The method of claim 3, further comprising, after the elongate distal portion of the tube is inserted into the patient's stomach, applying negative pressure is from the suction source to the patient's stomach to decompress the patient's stomach.

5. The method of claim 4, further comprising using the tube as a template or sizer to create a gastric sleeve.

6. The method of claim 1, further comprising directing a dye solution from a syringe or infusion tubing through the proximal end of the first arm.

7. The method of claim 1, further comprising directing air through the proximal end of the first arm to inflate the body cavity.

8. The method of claim 1, wherein when the distal portion of the tube is fully inserted into the patient, the lumen in the first arm is in flow communication with the lumen in the second arm at the proximal end of the tube at a location exterior to the patient.

9. The method of claim 1, wherein the valve is configured such that, only while the valve is in the open state, air flow through the valve into the lumens of the tube exceeding a specific velocity causes an audible signal to be emitted by the valve.

10. The method of claim 1, further comprising:
    providing an inflatable cuff in proximity to the distal end of the tube, the inflatable cuff having an interior in flow communication with a second lumen within the elongate distal portion of the tube through an aperture in a wall of the tube, and with a lumen of a third arm of the proximal portion of the tube, the third arm also comprises an additional valve; and
    selectively injecting air into and withdrawing air from the second lumen of the elongate distal portion of the tube to inflate and deflate the inflatable cuff, the additional valve preventing loss of air from the inflatable cuff when t inflatable cuff is not actively being inflated or deflated.

11. The method of claim 10, wherein the step of inserting the elongate distal portion of the tube into the body cavity comprises inserting the distal portion through the patient's nose or mouth, through the pharynx and esophagus into the patient's stomach, and wherein, after the distal portion of the tube is inserted into the stomach, negative pressure is applied from the suction source to the stomach to decompress the stomach, the method further comprising:
  inflating the inflatable cuff; and
  using the inflated cuff as a template or sizer to create a gastric pouch.

12. The method of claim 1, further comprising providing as the valve, a valve that is biased to the closed state in which ambient air is prevented from flowing through the valve into the lumens of the tube such that the valve changes to the open state in which the valve allows ambient air to flow through the valve into the lumens of the tube only when ambient air pressure exceeds air pressure within the lumens of the tube by the specified amount.

13. The method of claim 1, further comprising providing the valve with a spring that biases the valve to the closed state in which ambient air is prevented from flowing through the valve into the lumens of the tube such that the valve changes to the open state in which the valve allows ambient air to flow through the valve into the lumens of the tube only when ambient air pressure exceeds air pressure within the lumens of the tube by the specified amount.

14. The method of claim 1, wherein the elongate distal portion is elastomeric and tubular.

15. A method for introducing and maintaining a level of negative pressure in a patient's body cavity, the method comprising:
  inserting a distal portion of a gastric tube into the body cavity, the distal portion comprising a lumen and at least one aperture in proximity to a distal end, the tube including a proximal portion having
    a first arm comprising a lumen,
    a second arm comprising a lumen, and
    a common space in flow communication with the lumen of the distal portion and the lumens of the first and second arms and interposed between the lumens of the first and second arms and the lumen of the distal portion such that any flow from the lumens of the first and second arms to the lumen of the distal portion flows through the common space and any flow from the lumen of the distal portion to the lumens of the first and second arms flows through the common space;
  coupling a proximal end of the first arm via tubing to a suction source;
  applying, after the distal portion of the tube is inserted into the body cavity and the proximal end of the first arm is coupled to the suction source, negative pressure from the suction source to the body cavity through the lumen of the first arm, through the common space and through the lumen of distal portion and maintaining an intraluminal negative pressure in the tube greater than 80 mmHg; and
  providing a valve relative to the second arm to control the intraluminal negative pressure to be greater than 80 mmHg such that while the intraluminal negative pressure in the tube is greater than 80 mmHg:
    the valve does not allow passage of air therethrough when ambient air pressure exceeds air pressure within the lumens of the tube until a difference between the ambient air pressure and the intraluminal negative pressure exceeds a specified amount associated with the valve that is greater than 80 mmHg, and
    the difference between the ambient air pressure and the intraluminal negative pressure exceeding the specified amount causes the valve to change from a closed state in which ambient air is prevented from flowing through the valve into the lumens of the tube to an open state in which the valve allows ambient air to flow through the valve into the lumen of the second arm through the common space and into the lumen of the distal portion in order to limit the intraluminal negative pressure and the negative pressure within the body cavity to a pressure within a desirable range.

16. The method of claim 15, wherein the lumen of the distal portion has an open proximal end directly opening into the common space, the lumen of the first arm has an open distal end region directly opening into the common space, the lumen of the second arm has an open distal end region directly opening into the common space, and the distal portion includes only a single lumen.

17. The method of claim 15, wherein the valve is configured such that, only while the valve is in the open state, air flow through the valve into the lumens of the tube exceeding a specific velocity causes an audible signal to be emitted by the valve.

18. The method of claim 15, further comprising providing as the valve, a valve that is biased to the closed state in which ambient air is prevented from flowing through the valve into the lumens of the tube such that the valve changes to the open state in which the valve allows ambient air to flow through the valve into the lumens of the tube only when ambient air pressure exceeds air pressure within the lumens of the tube by the specified amount.

19. The method of claim 15, further comprising providing the valve with a spring that biases the valve to the closed state in which ambient air is prevented from flowing through the valve into the lumens of the tube such that the valve changes to the open state in which the valve allows ambient air to flow through the valve into the lumens of the tube only when ambient air pressure exceeds air pressure within the lumens of the tube by the specified amount.

20. A gastric tube through which negative pressure is applied into a body cavity and enables the negative pressure to be maintained in the body cavity at a level of at least 80 mmHg, the tube comprising:
  an elongate elastomeric tubular distal portion, insertable into the body cavity, comprising a lumen and at least one aperture in proximity to a distal end,
  a proximal portion having
    a first arm comprising a lumen,
    a second arm comprising a lumen, and
    a common space in flow communication with the lumen of said distal portion and the lumens of said first and second arms and interposed between the lumens of said first and second arms and the lumen of said distal portion such that any flow from the lumens of said first and second arms to the lumen of said distal portion flows through the common space and any flow from the lumen of said distal portion to the lumens of said first and second arms flows through said common space;
  a proximal end of said first arm, or a tubular extension therefrom, being adaptable to tubing from a suction source and through which the negative pressure from the suction source is applied to the body cavity through said distal portion, the lumens in said first and second arms being in flow communication with the lumen of said distal portion to enable an intraluminal negative pressure in the tube greater than 80 mmHg,
  a valve arrangeable relative to said second arm, said valve being configured such that while the intraluminal negative pressure is equal to or more negative than 80 mmHg, said valve does not allow passage of air therethrough until a difference between the ambient air pressure and the intraluminal negative pressure equals or exceeds a specified amount, and the difference between the ambient air pressure and the intraluminal negative pressure exceeding the specified amount causes said valve to change from a closed state in which ambient air is prevented from flowing through said valve into the lumens of the tube to an open state in which said valve allows ambient air to flow through said valve into the lumen of said second arm through the common space and into the lumen of said distal portion in order to reduce air pressure within the lumens of the tube and within the body cavity which is in flow communication with the lumens of the tube through the at least one aperture in proximity to said distal portion of the tube.

\* \* \* \* \*

UNITED STATES PATENT AND TRADEMARK OFFICE
CERTIFICATE OF CORRECTION

PATENT NO. : 11,006,957 B1
APPLICATION NO. : 16/231713
DATED : May 18, 2021
INVENTOR(S) : Arnold Leiboff Page 1 of 1

It is certified that error appears in the above-identified patent and that said Letters Patent is hereby corrected as shown below:

In the Claims

Claim 4, Column 12, Line 27, after "pressure", delete "is".

Claim 10, Column 12, Line 60, after "when", change "t" to --the--.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*